(12) United States Patent
Taguchi et al.

(10) Patent No.: US 9,098,135 B2
(45) Date of Patent: Aug. 4, 2015

(54) TABLET TERMINAL AND RECORDING MEDIUM

(71) Applicant: FUJITSU LIMITED, Kawasaki-shi, Kanagawa (JP)

(72) Inventors: Akinori Taguchi, Kawasaki (JP); Satoshi Nakashima, Kawasaki (JP); Masayoshi Shimizu, Hadano (JP); Sachiko Tsujigaki, Yokohama (JP); Takehiko Raku, Zama (JP); Yoshiro Munesada, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 103 days.

(21) Appl. No.: 13/868,523

(22) Filed: Apr. 23, 2013

(65) Prior Publication Data
US 2013/0307797 A1    Nov. 21, 2013

(30) Foreign Application Priority Data

May 18, 2012 (JP) .................................. 2012-114985

(51) Int. Cl.
*G06F 3/041* (2006.01)
*G06F 3/0488* (2013.01)
*G06F 3/01* (2006.01)
*G06F 3/0481* (2013.01)
*A61B 3/113* (2006.01)
*G06K 9/00* (2006.01)

(52) U.S. Cl.
CPC ............... *G06F 3/041* (2013.01); *A61B 3/113* (2013.01); *G06F 3/013* (2013.01); *G06F 3/0488* (2013.01); *G06F 3/04817* (2013.01); *G06F 3/04886* (2013.01); *G06K 9/00604* (2013.01)

(58) Field of Classification Search
USPC ................. 345/173, 156, 8, 157, 158, 7, 9; 348/158; 351/209; 463/32
See application file for complete search history.

(56) References Cited

U.S. PATENT DOCUMENTS

| 6,204,828 | B1 * | 3/2001 | Amir et al. .................... 345/7 |
| 6,578,962 | B1 * | 6/2003 | Amir et al. .................... 351/209 |
| 2005/0047629 | A1 * | 3/2005 | Farrell et al. ................ 382/117 |
| 2005/0243054 | A1 * | 11/2005 | Beymer et al. .............. 345/156 |

(Continued)

FOREIGN PATENT DOCUMENTS

WO    WO 99/22638    *    5/1999

OTHER PUBLICATIONS

Takashi Nagamatsu et al., "Mobi-Gaze: Development of a Gaze Interface for Handheld Mobile Devices," CHI 2010: Work-in-Progress, (2010), pp. 3349-3354.

*Primary Examiner* — Thuy Pardo
(74) *Attorney, Agent, or Firm* — Staas & Halsey LLP

(57) ABSTRACT

A tablet terminal receives a triggering indication to enable a detection result of eye gaze, and sets a target area in which the presence of a target object is assumed on a screen of a touch panel using a detection position of eye gaze. The tablet terminal further displays a partial image displayed in the target area out of an image displayed on the screen in an aiming area in which a touch operation to the target area is received in place of the target area, and records a correspondence relation between coordinates of the aiming area and coordinates of the target area. When a touch operation is received within the aiming area, the tablet terminal converts the coordinates of the aiming area in which the touch operation is received into the coordinates projected to the target area using the correspondence relation recorded, and then outputs the converted coordinates.

5 Claims, 12 Drawing Sheets

(56) References Cited

U.S. PATENT DOCUMENTS

| | | | |
|---|---|---|---|
| 2011/0170067 A1* | 7/2011 | Sato et al. | 351/209 |
| 2012/0019662 A1* | 1/2012 | Maltz | 348/158 |
| 2013/0050070 A1* | 2/2013 | Lewis et al. | 345/156 |
| 2013/0178287 A1* | 7/2013 | Yahav | 463/32 |
| 2013/0300653 A1* | 11/2013 | Lewis et al. | 345/156 |
| 2014/0049452 A1* | 2/2014 | Maltz | 345/8 |

* cited by examiner

FIG.8

| AIMING AREA COORDINATES | TARGET AREA COORDINATES |
|---|---|
| (xd0, yd0) | (xs0, ys0) |
| (xd1, yd0) | (xs1, ys0) |
| ⋮ | ⋮ |
| (xda, yda) | (xsa, ysa) |
| ⋮ | ⋮ |
| (xd(ll-1), ydls) | (xs(ll-1), ysls) |
| (xdll, ydls) | (xsll, ysls) |

TABLET TERMINAL AND RECORDING MEDIUM

CROSS-REFERENCE TO RELATED APPLICATION

This application is based upon and claims the benefit of priority of the prior Japanese Patent Application No. 2012-114985, filed on May 18, 2012, the entire contents of which are incorporated herein by reference.

FIELD

The embodiments discussed herein are related to a tablet terminal and an operation receiving program.

BACKGROUND

Tablet terminals including smartphones, cellular phones, personal handyphone systems (PHS), and personal digital assistants (PDA) have been widely used. To improve operability of such tablet terminals, a user interface that combines eye-gaze input and contact input has been developed.

In briefly explaining the foregoing, the user interface receives movement of a cursor displayed on a touch panel by the move of eye gaze of a user. When a given area on the touch panel is subsequently touched, the user interface then selects an object at which the cursor is aimed. In this way, the user interface tries to make the user operate the touch panel in a one-handed operation with a hand holding the tablet terminal. An example of such user interface is described in a non-patent document: T. Nagamatsu, et al., "MobiGaze: Development of a Gaze Interface for Handheld Mobile Devices", CHI 2010: Work-in-Progress, Apr. 12-13, 2010.

The above-described conventional technology, however, may increase a strain on the eyes of the user as described in the following.

More specifically, when a human sees things, the eye gaze does not stay at a certain place and generally moves around the periphery of a target, and thus fixing the eye gaze may cause an eye strain. The above-described user interface, however, forces to fix the eye gaze on the cursor so as to move the cursor to the target object. As a result, the above-described user interface is likely to increase the strain on the eyes of the user. Furthermore, when aiming the cursor to the target object by eye gaze, as the target object becomes smaller, the user may move the eye gaze more minutely. As a consequence, depending on the size of the object displayed on the touch panel, the strain on the eyes of the user may further be increased.

SUMMARY

According to an aspect of an embodiment, a tablet terminal includes a memory, and a processor coupled to the memory. The processor executes a process including: receiving a triggering indication to enable a detection result of eye gaze; setting a target area in which presence of a target object is assumed on a screen of a touch panel using a detection position of eye gaze; displaying a partial image displayed in the target area out of an image displayed on the screen in an aiming area in which a touch operation to the target area is received in place of the target area; recording a correspondence relation between coordinates of the aiming area and coordinates of the target area in a storage unit; converting coordinates of the aiming area in which a touch operation is received into coordinates projected to the target area using the correspondence relation stored in the storage unit when the touch operation is received in the aiming area; and outputting the converted coordinates.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 8 is a table illustrating an example of correspondence relation information;

DESCRIPTION OF EMBODIMENTS

Preferred embodiments will be explained with reference to accompanying drawings. The embodiments, however, are not intended to restrict the technology disclosed. Each of the embodiments can be combined appropriately within a range not making the content of process inconsistent.

[a] First Embodiment

Configuration of Tablet Terminal

Figure 1:
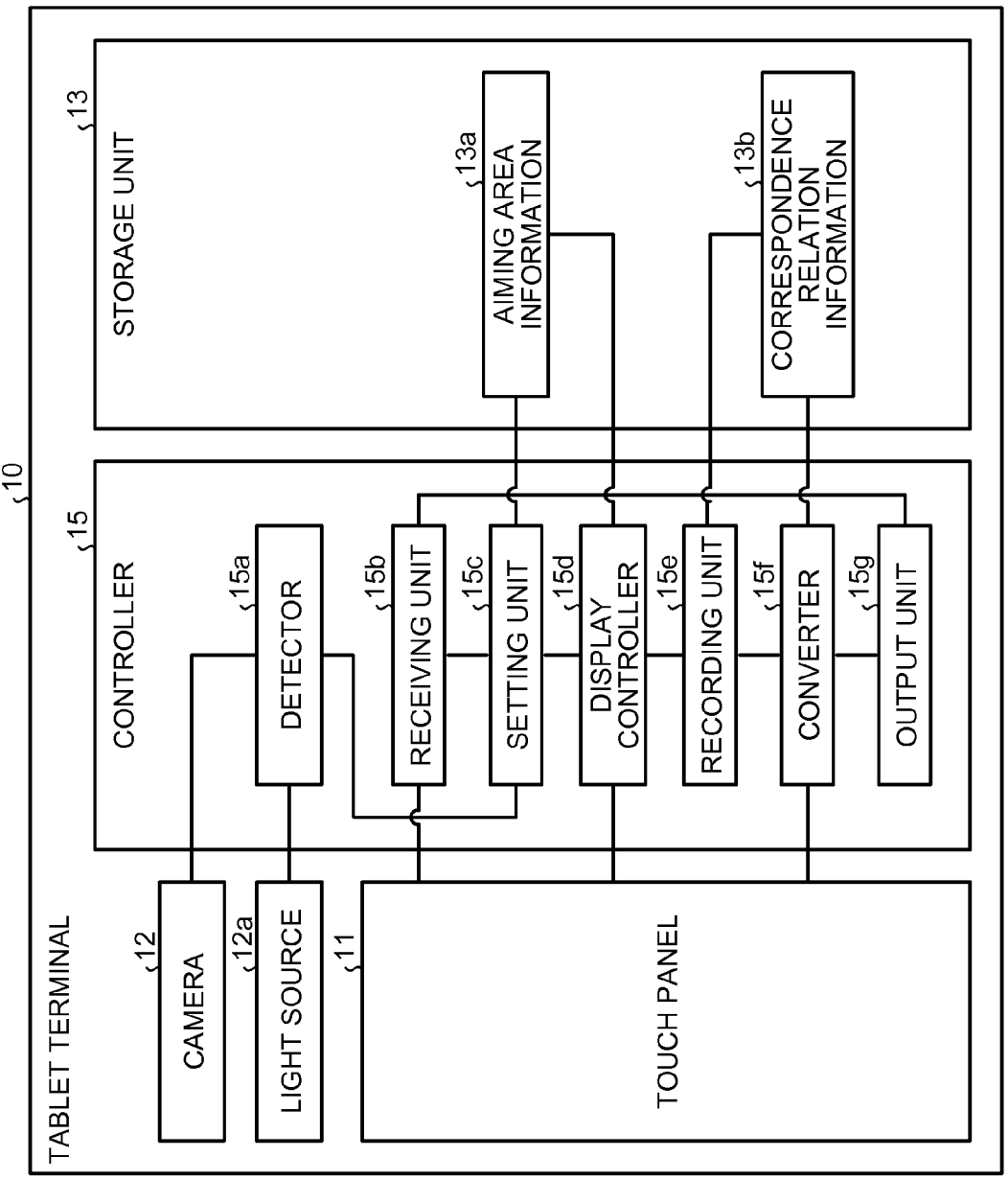
FIG. 1 is a block diagram illustrating a functional configuration of a tablet terminal according to a first embodiment.

FIG. 1 is a block diagram illustrating a functional configuration of a tablet terminal according to a first embodiment. A tablet terminal 10 illustrated in FIG. 1 is a device that combines a touch operation to a screen and detection of eye gaze to specify a position on the screen of a touch panel 11, and in particular, to make a user operate the touch panel in a one-handed operation with a hand holding the tablet terminal 10.

Such tablet terminal 10 can be implemented by installing the operation receiving program that executes the above-described operation receiving process to an information-processing terminal including a cellular phone represented by a smartphone, and a PHS, a PDA, and the like. The above-described PHS is an abbreviation of Personal Handyphone System, and the PDA is an abbreviation of Personal Digital Assistant.

The tablet terminal 10 in the first embodiment displays a partial image of a target area in which a detected position of eye gaze points on the screen of the touch panel 11 in an aiming area on the side close to hand so that the tablet terminal 10 receives an operation in a range not reachable by the hand holding the terminal.

Figure 2:
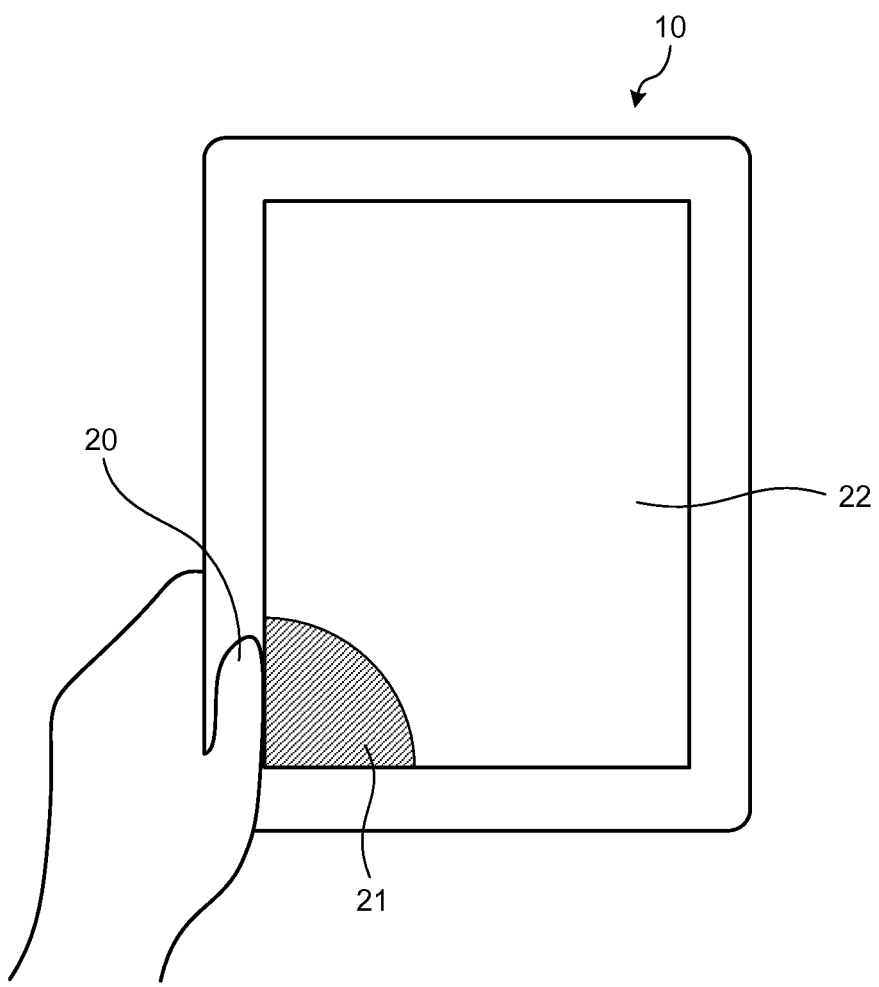
FIG. 2 is a diagram illustrating an example of an area operable in a touch operation and an area difficult to operate in a touch operation with a hand holding the tablet terminal.

More specifically, it is difficult to receive specification of positions over the entire screen of the touch panel 11 only by a touch operation with one hand. FIG. 2 is a diagram illustrating an example of an area operable in a touch operation and an area difficult to operate in a touch operation with the hand holding the tablet terminal. As illustrated in FIG. 2, when the user makes a one-handed operation on the touch panel with the hand holding the tablet terminal 10, the range of screen that can be touched by fingers of the hand holding the touch panel 11, typically a thumb 20, is an area 21 in which the touch operation is feasible. In contrast, the range that is difficult to be touched by the thumb 20 of the hand holding the tablet terminal 10 is an area 22 that is difficult to make the touch operation. As in the foregoing, because the range that the thumb 20 can make contact on the screen is limited under the condition of the base of the thumb 20 being fixed by holding the tablet terminal 10, it is difficult to specify positions over the entire screen of the touch panel 11 only by the touch operation.

The tablet terminal 10 thus uses the advantage of eye-gaze input and the advantage of contact input combined to make the touch operation feasible on a target object without gazing at one point of the target object.

In explaining the foregoing, the tablet terminal 10 receives a triggering indication to enable a detection result of eye gaze. By making the user indicate the timing to enable the detection result of eye gaze in this manner, the position of eye gaze detected under a condition in which the eyes are turned to the periphery of a target object is used at a later stage of a process.

Figure 3:
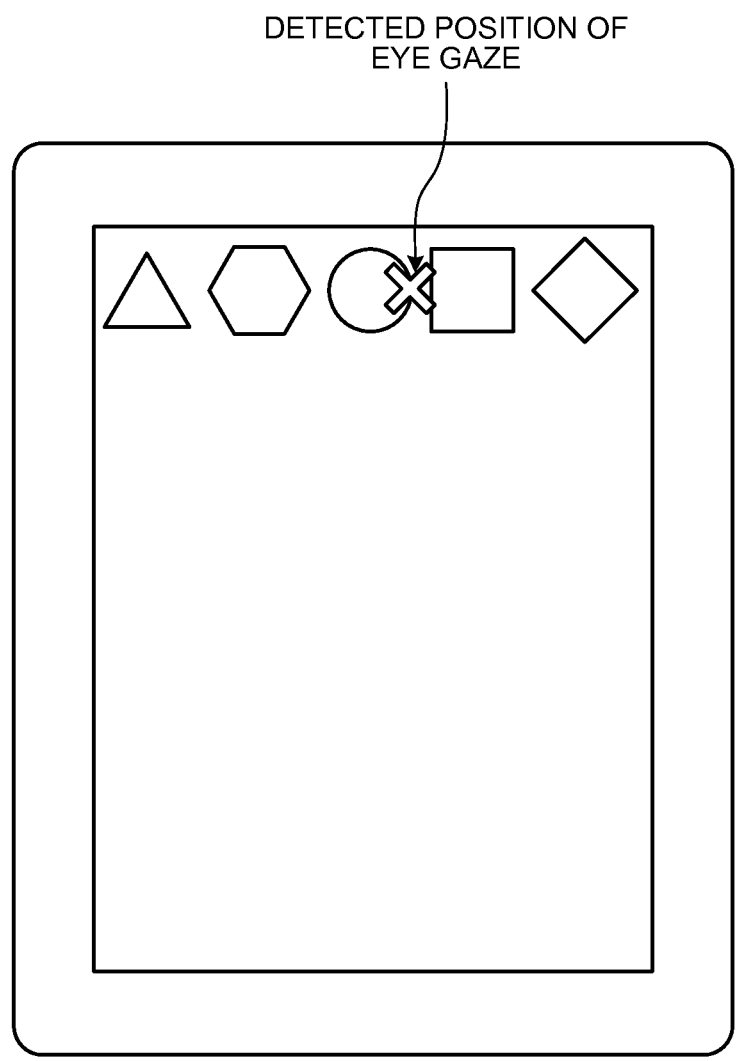
FIG. 3 is a diagram illustrating an example of a screen displayed on a touch panel.

The tablet terminal 10 then sets up a target area in which the presence of the target object on the screen is assumed based on the detected position of eye gaze obtained by eye-gaze detection. FIG. 3 is a diagram illustrating an example of the screen displayed on the touch panel 11. The example in FIG. 3 assumes that the user intends to select a round object out of five kinds of objects displayed on the touch panel 11 while holding the tablet terminal 10 with his/her left hand. As illustrated in FIG. 3, when the round object on the screen of the touch panel 11 is targeted, although the eye gaze of the user does not always be positioned on the round object, the eye gaze is highly likely to be positioned at the periphery of the round object. The tablet terminal 10, therefore, does not specify one point on the screen by viewpoint tracking but uses the eye-gaze detection to roughly specify an area indicating the presence of the target object.

Figure 4:
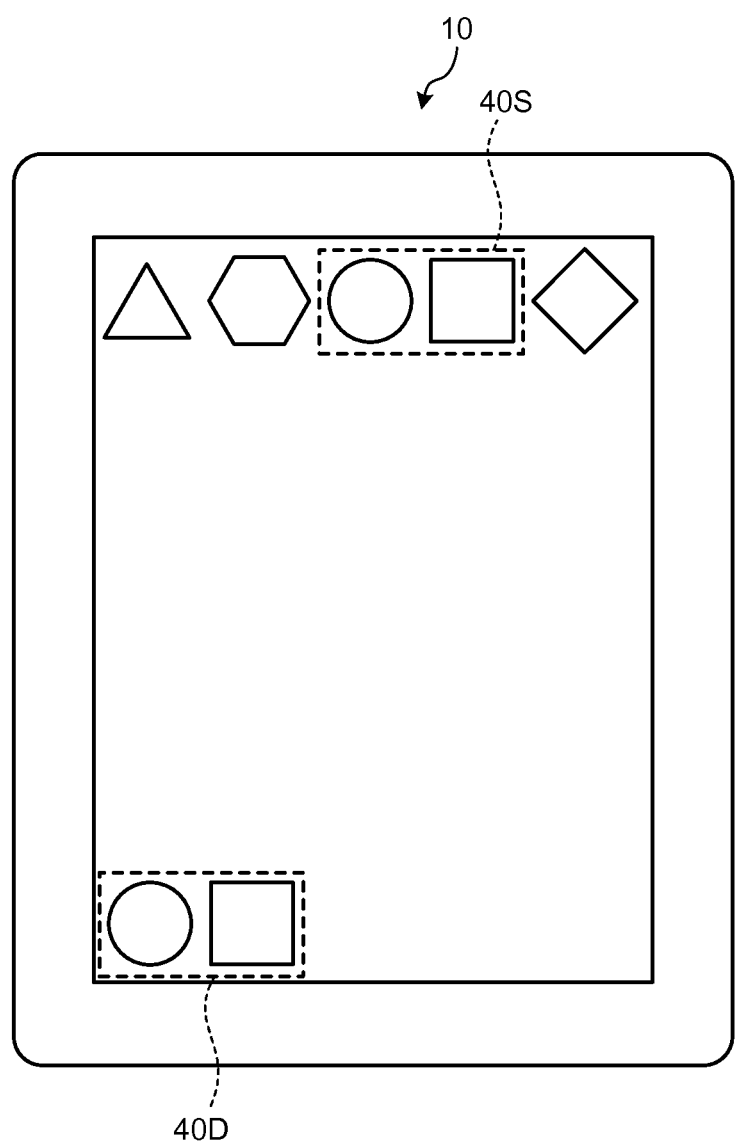
FIG. 4 is a diagram illustrating an example of a partial image in a target area displayed in an aiming area.

The tablet terminal 10 subsequently displays a partial image, which is displayed in the target area out of an image displayed on the screen, in an aiming area in which the touch operation to the target area is received in place of the target area. The aiming area is used as a window to aim the touch operation at the target object, instead of making the touch operation directly specify the partial image displayed in the target area. FIG. 4 is a diagram illustrating an example of the partial image in the target area displayed in the aiming area. As illustrated in FIG. 4, the partial image of a target area 40S, which includes the round object on which the user can lay his/her eyes but has difficulty performing the touch operation, is displayed in an aiming area 40D that the user is able to touch with the hand holding the tablet terminal 10. Consequently, the tablet terminal 10 makes the user specify one point by a touch operation out of the area roughly specified by the eye-gaze detection.

When the touch operation is subsequently received within the aiming area, the tablet terminal 10 converts the coordinates of the aiming area in which the touch operation is received into the coordinates projected to the target area using a correspondence relation between the coordinates of the aiming area and the coordinates of the target area, and then outputs the converted coordinates. This allows the touch operation made on the partial image displayed in the aiming area to be identified and received as the operation being made on the partial image displayed in the target area.

As in the foregoing, the tablet terminal 10 in the first embodiment displays the partial image of the target area in which the detected position of eye gaze points on the screen of the touch panel 11 in the aiming area on the side close to hand so that the tablet terminal 10 receives the operation in a range not reachable by the hand holding the terminal. The tablet terminal 10 in the first embodiment thus enables the touch operation to be made on the target object without gazing at one point of the target object when a one-handed operation is made on the touch panel with the hand holding the tablet terminal 10. Consequently, the tablet terminal 10 in the first embodiment can relieve the strain on the eyes of the user.

Returning to the explanation of FIG. 1, the tablet terminal 10 includes the touch panel 11, a camera 12, a light source 12a, a storage unit 13, and a controller 15. The tablet terminal 10 may include, other than those functional units depicted in FIG. 1, various functional units that a known tablet terminal includes, for example, an antenna, a carrier communication unit that performs communication via a carrier network, and a microphone that collects voice.

The touch panel 11 is a device that allows for displaying and inputting. As one aspect, the touch panel 11 displays images output by an operating system (OS) and application programs executed by the controller 15 described later. As another aspect, the touch panel 11 receives a touch operation performed on the screen such as tap, flick, sweep, pinch close, and pinch open.

The camera 12 is an imaging device that uses a charge coupled device (CCD), a complementary metal-oxide semiconductor (CMOS), and the like. As one aspect, the camera 12 controls the light source 12a disposed near the camera 12 to irradiate a subject with infrared light, and upon receiving the light reflected from the subject, the camera 12 outputs an image of the subject being converted into a digital signal to a detector 15a described later. At this time, when the subject includes an eyeball of the user, the camera 12 catches the reflection of light from the retina and can obtain an image that shows a pupil portion of the eyeball appearing brighter than the other portions. For the camera 12, the camera mounted on the tablet terminal 10 before shipping may be appropriated, or an externally connected digital camera and the like can be used.

The storage unit 13 is a storage device that stores therein various programs such as the OS and the operation receiving program executed by the controller 15. The storage unit 13 includes, as one aspect, a semiconductor memory such as a flash memory, and a storage device such as a hard disk and an optical disk. The storage unit 13 is not restricted to the above-described types of storage devices, and may be a random access memory (RAM) and a read only memory (ROM). The storage unit 13 stores therein, as examples of data used for the programs executed by the controller 15, aiming area information 13a and correspondence relation information 13b which will be described later.

The controller 15 has an internal memory to store therein programs defining procedures of various processes and control data, and executes the various processes with the foregoing. The controller 15 includes, as illustrated in FIG. 1, the detector 15a, a receiving unit 15b, a setting unit 15c, a display controller 15d, a recording unit 15e, a converter 15f, and an output unit 15g.

The detector 15a out of the foregoing is a processor that performs eye-gaze detection of eyes. As one aspect, the detector 15a applies algorithm such as corneal reflection method to the image of the subject output from the camera 12, and detects the position of viewpoint at which the direction of eye gaze points from the center position of pupil of the eyeball, i.e., what is known as the point of gaze. In the following description, the position of viewpoint detected by the detector 15a may be referred to as the detected position of eye gaze. The detector 15a then outputs the position of eye gaze detected from the image of the subject to the setting unit 15c described later.

While detecting the position of eye gaze using the corneal reflection method is illustrated and described here, the position of eye gaze can be detected using other methods. For example, the disclosed device divides the screen of the touch panel 11 into areas, and learns the shapes of eyes looking at the divided areas, and then performs template matching with the shapes of eyes detected from the image of the subject received from the camera 12, thereby enabling the disclosed device to detect the position of eye gaze. Furthermore, the disclosed device may make the user wear a headset that detects the position of eye gaze, and may obtain the position of eye gaze detected by the headset.

The receiving unit 15b is a processor that receives an indication of timing to enable the result of eye gaze detected by the detector 15a. As one aspect, the receiving unit 15b can assume that the indication of timing is received when the touch panel 11 is tapped at the position within the screen of the touch panel 11 and away from the detected position of eye gaze by a distance equal to or greater than a given distance. As another aspect, the receiving unit 15b can assume that the indication of timing is received when a given touch operation, for example, a sweep is made on the screen of the touch panel 11. As yet another aspect, the receiving unit 15b can assume that the indication of timing is received when a button for timing indication displayed on the screen of the touch panel 11 is tapped. As another aspect, the receiving unit 15b can assume that the indication of timing is received when the recognition result of voice received from a sound collecting device such as a microphone not depicted matches a given keyword, for example, start.

The setting unit 15c is a processor that sets up a target area in which the presence of a target object is assumed on the screen of the touch panel 11 using the position of eye gaze detected by the detector 15a. As one aspect, the setting unit 15c sets up the detected position of eye gaze as the center of gravity of the target area, and sets up the width and height of the aiming area defined in the aiming area information 13a stored in the storage unit 13 as the width and height of the target area.

Figure 5:
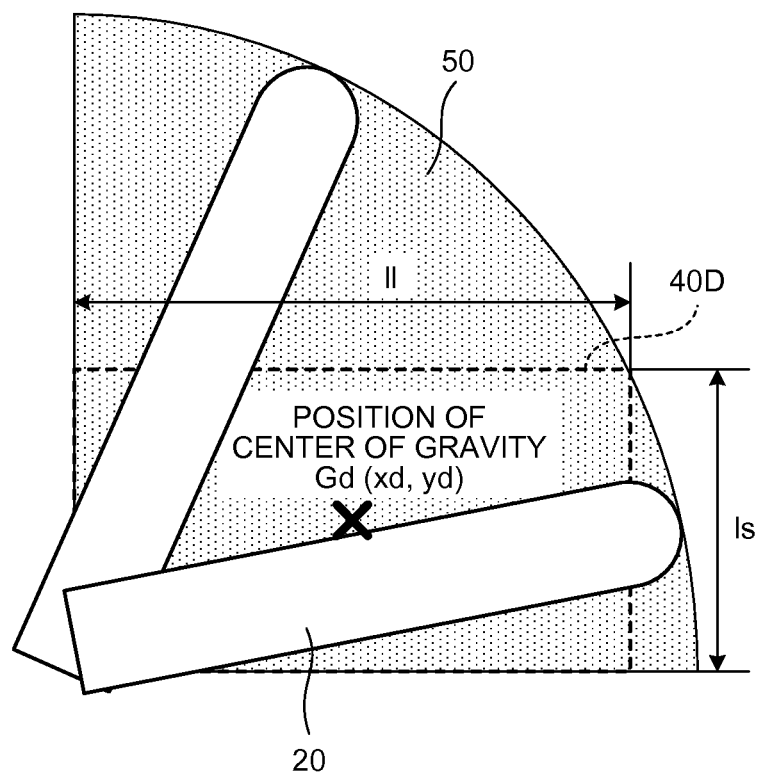
FIG. 5 is a diagram illustrating an example of the aiming area.

With reference to FIG. 5, the aiming area to superpose the detected position of eye gaze will now be described. FIG. 5 is a diagram illustrating an example of the aiming area. As illustrated in FIG. 5, the aiming area 40D is defined by the position of the center of gravity Gd (xd, yd) at which the center of gravity of the aiming area 40D resides on the screen of the touch panel 11, and by a width II and a height Is of the aiming area 40D. The aiming area 40D is defined in a shape and size equal to or smaller than a range 50 that the thumb 20 of the hand of the user can reach while holding the tablet terminal 10. In the example in FIG. 5, a rectangular area that is included in the range 50 and is adjacent to a corner portion of the tablet terminal 10 is defined as the aiming area 40D. At this time, when the up-down direction of the image displayed on the screen of the touch panel 11 is fixed, the position of the center of gravity Gd (xd, yd) can be defined such that the lower left corner of the image displayed and the lower left vertex of the aiming area 40D match up.

While the shape of the aiming area 40D is illustrated and described to be rectangular in the example in FIG. 5, the aiming area 40D may be in other shapes, for example, polygonal other than a quadrangle, round, or oblong. Furthermore, the aiming area 40D is not necessarily fixed, and the position of the center of gravity, the width, and the height can be calibrated in response to the length of thumb of the user.

Figure 6:
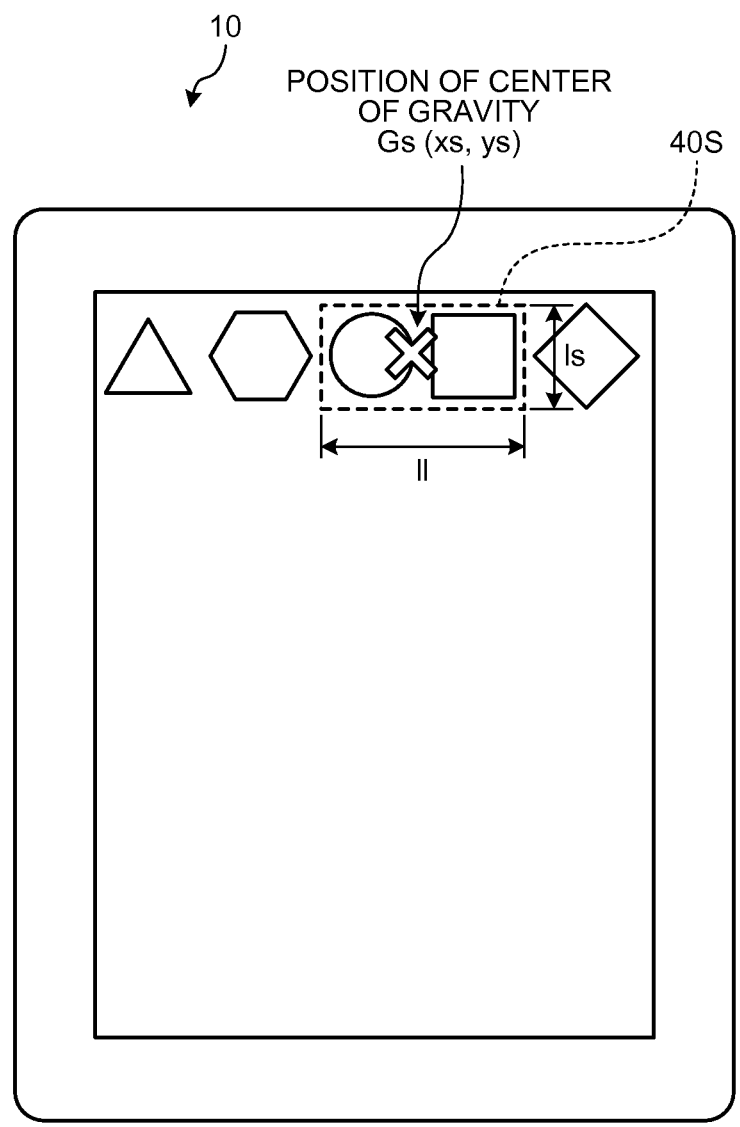
FIG. 6 is a diagram illustrating a setting example of the target area.

With reference to FIG. 6, the method of setting up a target area will be described. FIG. 6 is a diagram illustrating a setting example of the target area. As illustrated in FIG. 6, the detected position of eye gaze (xs, ys) is set as the position of the center of gravity Gs (xs, ys) of the target area 40S, and the width II and the height Is of the aiming area 40D are set as the width and height of the target area 40S. While the size of the target area 40S and that of the aiming area 40D set up in the example in FIG. 6 are illustrated and described to be the same, the both sizes are not necessarily the same. For example, when a partial image displayed in the target area 40S is displayed in the aiming area being enlarged, the width and height of the target area 40S can be set by reducing the width and height of the aiming area 40D corresponding to the enlargement factor of the partial image.

The display controller 15d is a processor that performs display control of the touch panel 11. As one aspect, the display controller 15d displays a partial image displayed in the target area out of an image displayed on the screen in the aiming area in which the touch operation to the target area is received in place of the target area. As a result, as illustrated in FIG. 4, the partial image of the target area 40S, which includes the round object on which the user can lay his/her eyes but has difficulty performing the touch operation, is displayed in the aiming area 40D that the user can touch with the hand holding the tablet terminal 10.

Figure 7:
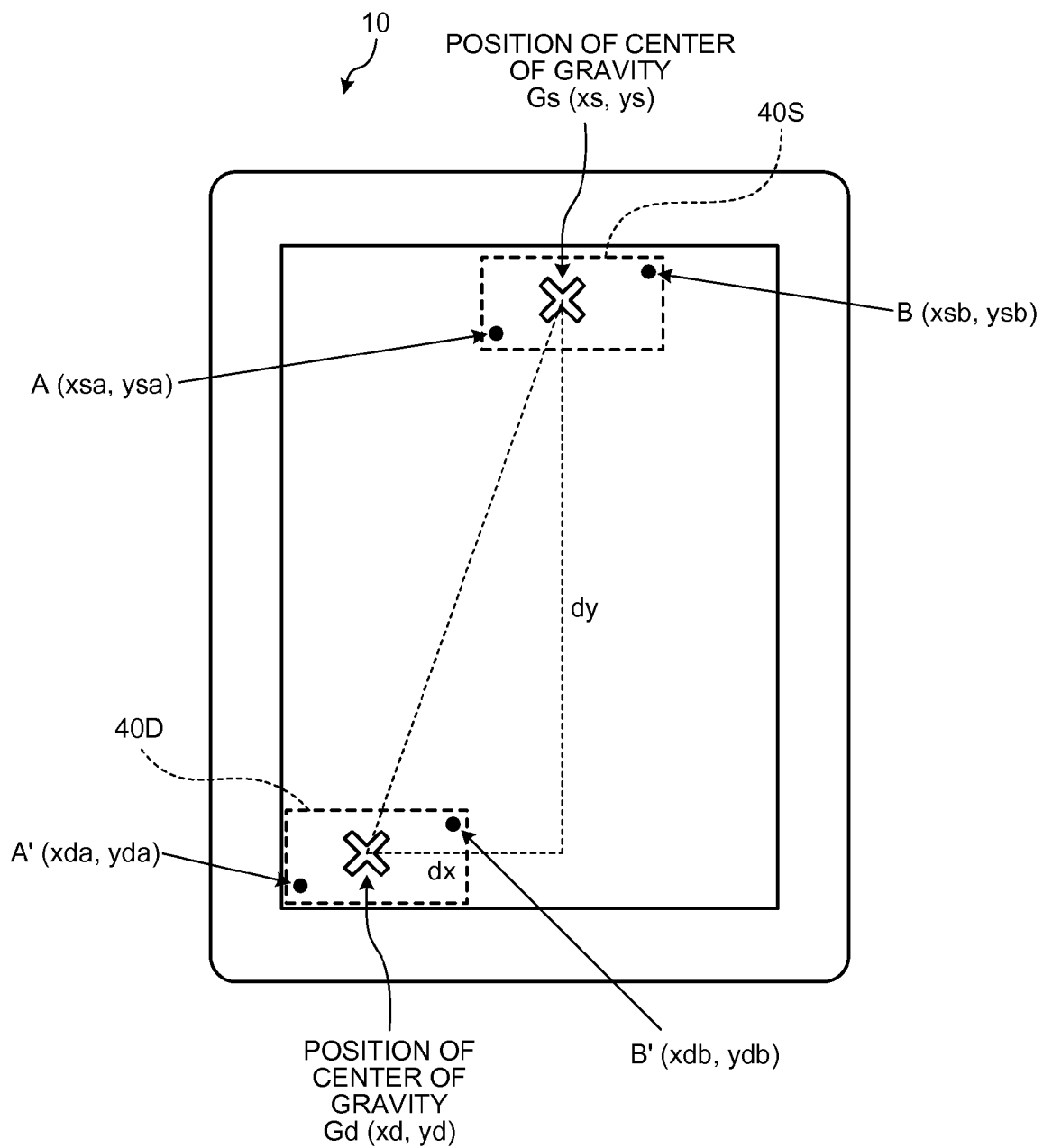
FIG. 7 is a diagram illustrating an example of a method of correlating coordinates of the aiming area and coordinates of the target area.

The recording unit 15e is a processor that records the correspondence relation between the coordinates of aiming area and the coordinates of target area in the storage unit 13. As one aspect, the recording unit 15e calculates the difference (dx, dy) in position between the coordinates of the center of gravity Gs (xs, ys) of the target area and the coordinates of the center of gravity Gd (xd, yd) of the aiming area. The recording unit 15e then substitutes the coordinates of each pixel included in the aiming area into a conversion function expressed by the difference in position (dx, dy) calculated so as to derive the coordinates of each pixel included in the target area. FIG. 7 is a diagram illustrating an example of a method of correlating the coordinates of the aiming area and the coordinates of the target area. As illustrated in FIG. 7, performing the subtraction (xs−xd, ys−yd) to subtract the coordinates of the center of gravity Gd (xd, yd) of the aiming area 40D from the coordinates of the center of gravity Gs (xs, ys) of the target area 40S calculates the difference in position (dx, dy). Thereafter, the coordinates of each pixel included in the aiming area 40D are substituted into the conversion function expressed by the difference in position (dx, dy). For example, adding the difference in position (dx, dy) to the coordinates of a pixel A' (xda, yda) included in the aiming area 40D calculates the coordinates of a pixel A (xsa, ysa) in the target area 40S. Furthermore, adding the difference in position (dx, dy)

to the coordinates of a pixel B' (xdb, ydb) included in the aiming area 40D calculates the coordinates of a pixel B (xsb, ysb) in the target area 40S. In this way, the coordinates of each pixel included in the target area are calculated.

The recording unit 15e then generates the correspondence relation information 13b in which the coordinates of each pixel included in the aiming area and the coordinates of each pixel included in the target area are correlated to each other, and subsequently records the correspondence relation information 13b in the storage unit 13. FIG. 8 is a table illustrating an example of the correspondence relation information 13b. The example in FIG. 8 indicates that the coordinates (xd0, yd0), (xd1, yd0), ..., (xdII, ydIs) of the pixels included in the aiming area 40D correspond to the coordinates (xs0, ys0), (xs1, ys0), ..., (xsII, ysIs) of the pixels included in the target area 40S, respectively. While the correspondence relation information 13b is illustrated and described as the correspondence relation between the coordinates of each pixel included in the aiming area and the coordinates of each pixel included in the target area in the example in FIG. 8, the conversion function expressed by the difference in position (dx, dy) may be recorded as the correspondence relation information 13b.

The converter 15f is a processor that converts, when a touch operation is received within the aiming area, the coordinates of the aiming area in which the touch operation is received into the coordinates projected to the target area using the correspondence relation information 13b. As one aspect, the converter 15f monitors a tap operation from when displaying of a partial image of the target area in the aiming area is started by the display controller 15d until a given period of time td, for example, five seconds, elapses. At this time, when a tap operation is made within the given period of time, the converter 15f further determines whether the coordinates at which the tap operation is made are within the aiming area. When the coordinates of the tap operation are within the aiming area, the converter 15f converts the coordinates of the tap operation in the aiming area into the coordinates of the target area corresponding to the coordinates of the tap operation in the aiming area out of the coordinates of the target area defined in the correspondence relation information 13b. At this time, when the conversion function expressed by the difference in position (dx, dy) is recorded as the correspondence relation information 13b, the converter 15f may convert the coordinates of the tap operation in the aiming area into the coordinates of the target area by adding the difference in position (dx, dy) to the coordinates of the aiming area.

Figure 9:
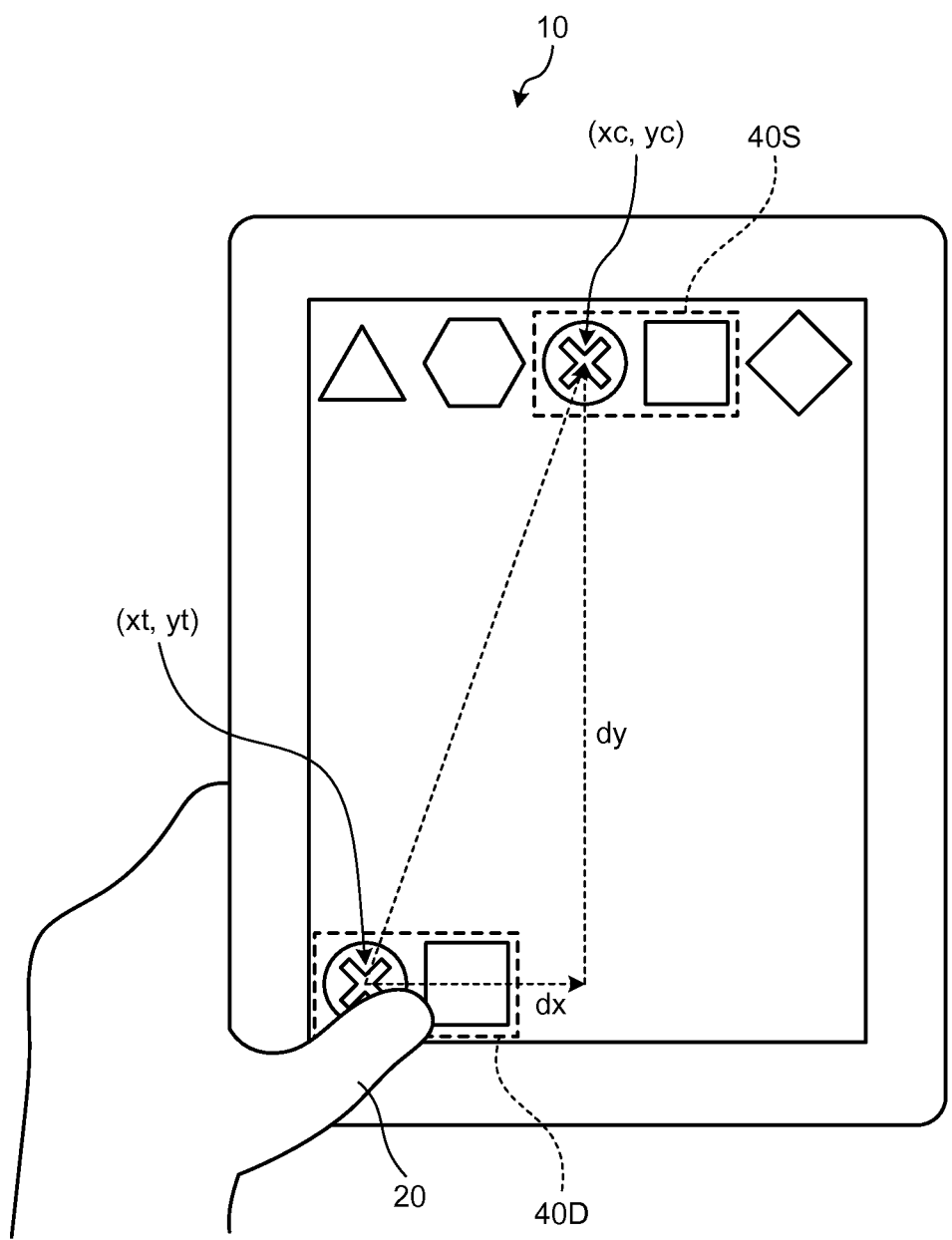
FIG. 9 is a diagram illustrating an example of coordinate conversion.

FIG. 9 is a diagram illustrating an example of coordinate conversion. For example, as illustrated in FIG. 9, when a tap operation is made at coordinates (xt, yt) in the aiming area 40D, the coordinates of the tap operation (xt, yt) are converted into the coordinates (xc, yc) that include the difference in position (dx, dy) added. This allows the tap operation made on a partial image displayed in the aiming area to be identified as the tap operation made on the partial image displayed in the target area.

The output unit 15g is a processor that outputs the coordinates of the target area converted by the converter 15f to a given destination. As one aspect, the output unit 15g outputs the coordinates of the target area converted by the converter 15f to the OS and application programs executed by the controller 15. Such output of the coordinates of the target area makes the OS and the application programs recognize that the user tapped, in the example illustrated in FIG. 9, the round object that is the target of an operation. While tapping an icon as one example of objects is assumed in the example in FIG. 9, a similar effect can be achieved when other objects, for example, a tab, a pull-down menu, and a link are tapped.

As for the controller 15, various integrated circuits and electronic circuits can be adopted. Furthermore, a part of the functional units of the controller 15 can be made as a separate integrated circuit or electronic circuit. For example, the integrated circuit includes an application specific integrated circuit (ASIC). The electronic circuit includes a central processing unit (CPU) and a micro processing unit (MPU).

Processing Flow

Figure 10:
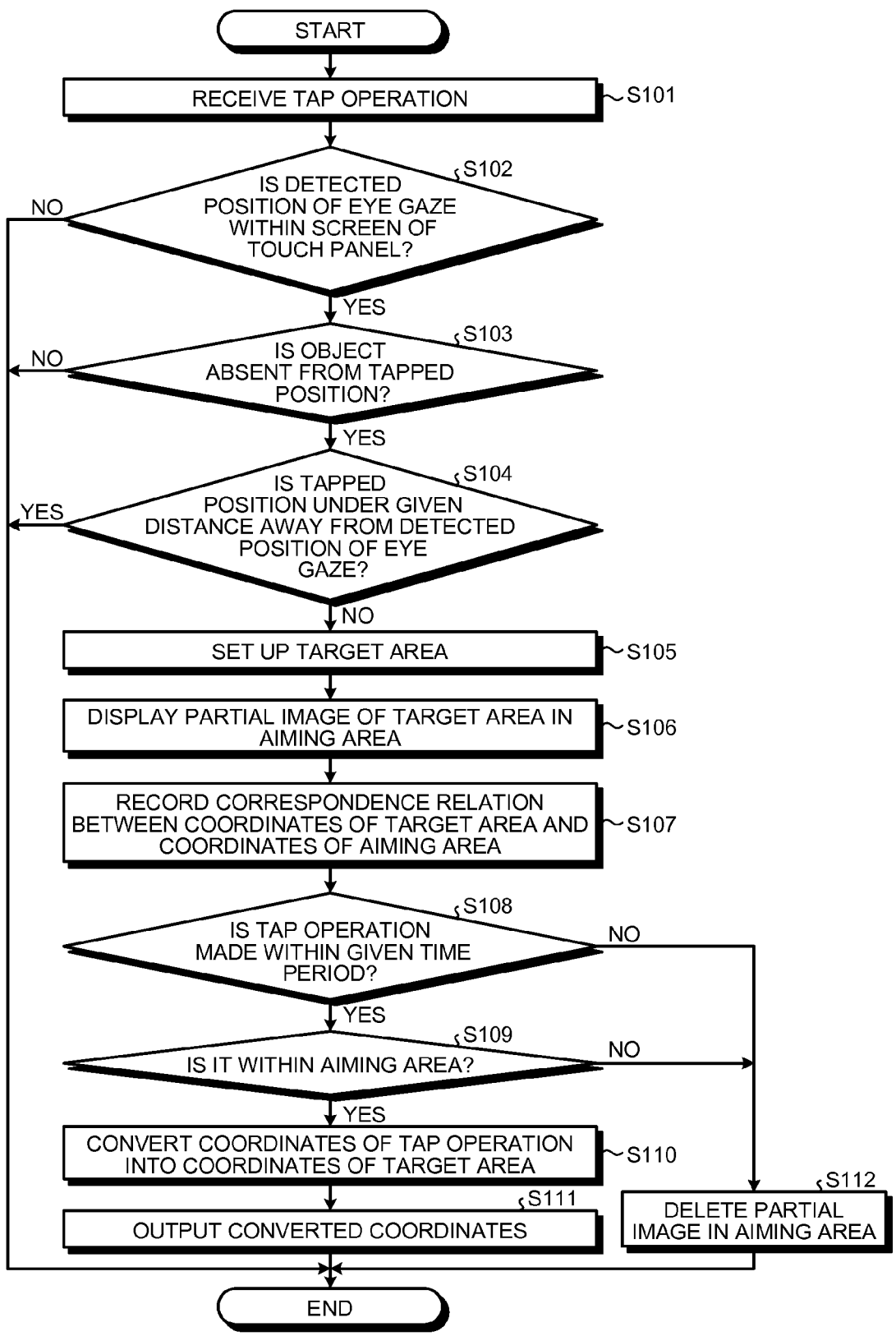
FIG. 10 is a flowchart illustrating a procedure for an operation receiving process in the first embodiment.

FIG. 10 is a flowchart illustrating a procedure for the operation receiving process in the first embodiment. The operation receiving process is a process repeatedly executed as long as the tablet terminal 10 is powered on, and is started when a tap operation on the screen of the touch panel 11 is received.

As illustrated in FIG. 10, when a tap operation is received on the screen of the touch panel 11 (Step S101), the tablet terminal 10 determines whether the detected position of eye gaze is within the screen of the touch panel 11 (Step S102).

At this time, when the detected position of eye gaze is not within the screen of the touch panel 11 (No at Step S102), it can be assumed that the user is turning his/her eyes away and is not likely to have an intention to operate the tablet terminal 10. In this case, the tablet terminal 10 ends the process without executing subsequent processes any further.

In contrast, when the detected position of eye gaze is within the screen of the touch panel 11 (Yes at Step S102), the tablet terminal 10 determines whether an object is absent from the position at which the tap operation is received (Step S103).

When an object is present at the position of the tap operation received (No at Step S103), the tablet terminal 10 ends the process after when the coordinates of the tap operation received are output to the program outputting the object.

When an object is not present at the position of the tap operation received (Yes at Step S103), the tablet terminal 10 determines whether the position of the tap operation received is under a given distance away from the detected position of eye gaze. When the position of the tap operation received is under the given distance away from the detected position of eye gaze (Yes at Step S104), the tablet terminal 10 ends the process without executing subsequent processes any further.

At this time, when the position of the tap operation received is equal to or greater than the given distance away from the detected position of eye gaze (No at Step S104), the tablet terminal 10 executes the following process. More specifically, the tablet terminal 10 uses the position of eye gaze detected at the time the tap operation is received at Step S101 to set up a target area in which the presence of a target object is assumed on the screen of the touch panel 11 (Step S105).

The tablet terminal 10 subsequently displays a partial image, which is displayed in the target area out of the image displayed on the screen, in an aiming area in which the touch operation to the target area is received in place of the target area (Step S106).

The tablet terminal 10 then generates the correspondence relation information 13b in which the coordinates of each pixel included in the aiming area and the coordinates of each pixel included in the target area are correlated, and subsequently records the correspondence relation information 13b in the storage unit 13 (Step S107).

The tablet terminal 10 then monitors a tap operation from when displaying of the partial image of the target area in the aiming area is started at Step S106 until the given period of time td, for example, five seconds, elapses (Step S108).

When the tap operation is made within the given period of time (Yes at Step S108), the tablet terminal 10 further determines whether the coordinates at which the tap operation is made are within the aiming area (Step S109).

When the coordinates of the tap operation are within the aiming area (Yes at Step S109), the tablet terminal 10 executes the following process. More specifically, the tablet terminal 10 converts the coordinates of the tap operation in the aiming area into the coordinates of the target area corresponding to the coordinates of the tap operation in the aiming area out of the coordinates of the target area defined in the correspondence relation information 13b (Step S110). Thereafter, the tablet terminal 10 outputs the coordinates of the target area converted at Step S110 to the OS and application programs (Step S111), and ends the process.

Meanwhile, when the tap operation is not made within the given period of time (No at Step S108) or when the coordinates of the tap operation are not within the aiming area (No at Step S109), the tablet terminal 10 executes the following process. More specifically, the tablet terminal 10 deletes the partial image displayed in the aiming area at Step S106 (Step S112), and ends the process.

While it is illustrated and described that the process at Step S107 is executed after the process at Step S106 is executed in the above-described flowchart, the order of the processes at Step S106 and Step S107 can be interchanged with each other or the processes can be executed in parallel.

Effects of First Embodiment

As in the foregoing, the tablet terminal 10 in the first embodiment displays the partial image of the target area, at which the detected position of eye gaze points on the screen of the touch panel 11, in the aiming area on the side close to hand so as to receive the operation in a range not reachable by the hand holding the terminal. The tablet terminal 10 in the first embodiment therefore enables the touch operation to be made on the target object without gazing at one point of the target object when a one-handed operation is made on the touch panel with the hand holding the tablet terminal 10. Consequently, the tablet terminal 10 in the first embodiment can relieve the strain on the eyes of the user.

[b] Second Embodiment

While the embodiment of the disclosed apparatus has been described above, the present invention may be implemented in various different embodiments other than the above-described embodiment. The following description explains other embodiments that fall within the invention.

Application of Target Area Setting

While it has been illustrated and described that the position of eye gaze, which is detected at the time the timing is indicated by the tap operation, is used for setting the target area in the first embodiment, the position of eye gaze that is detected before the timing is indicated can be used for setting the target area.

More specifically, when a tap operation is used as a trigger to start the process, the tablet terminal 10 may shake as caused by the shock from the tap operation. This may lead to the deviation in the position of eye gaze detected before and after the tap operation is received. Meanwhile, it is assumed that the user is highly likely to prepare to look at the target object before making the tap operation. The disclosed apparatus therefore uses the position of eye gaze detected at the time before the tap operation is made for setting up the target area. Consequently, even when the tablet terminal 10 shakes as caused by the shock from the tap operation, the target area can be set up including the object that the user defines as the target.

Application of Resetting Target Area

The disclosed apparatus can calculate a ratio of difference in an image displayed on the screen of the touch panel 11 before and after the coordinates of the target area are output. When the ratio of difference in the image is equal to or smaller than a given threshold, the apparatus can further set up the area in which the image that represents the difference is displayed as a target area. Consequently, when the menu is displayed hierarchically, the hierarchically displayed menu can be selected in sequence.

The foregoing threshold is set to a ratio to the degree that whether a window screen output to the screen by an application program itself is changed or a part of display area such as a tab and a pull-down menu appeared on the window can be determined, for example, 50% of screen. When resetting the target area, the area displaying an image that represents the difference is reset as the target area even when the width and height of the image that represents the difference are greater than those in the aiming area information 13a, and the width and height of the aiming area are matched to those of the target area.

Figure 11:
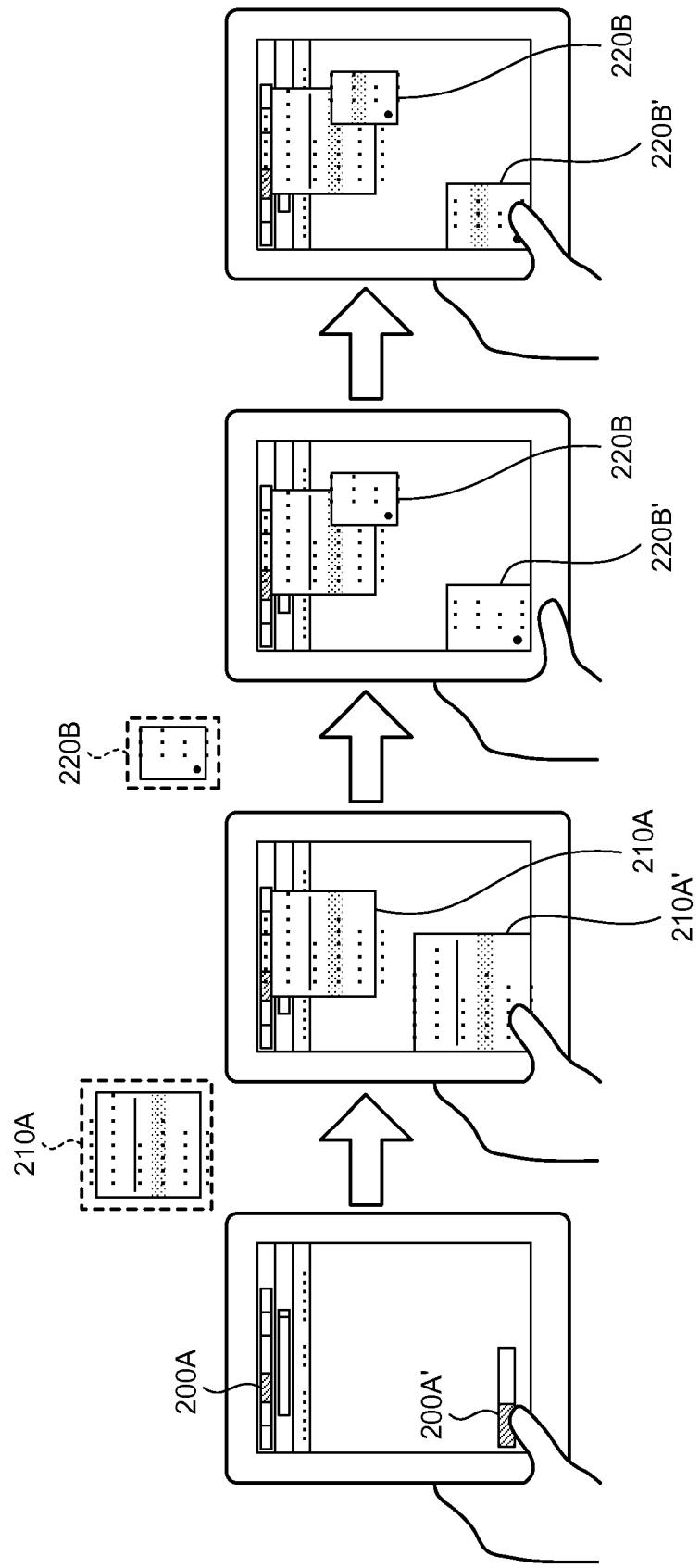
FIG. 11 is a diagram for explaining an example of application.

FIG. 11 is a diagram for explaining an example of the application. As illustrated in FIG. 11, while a menu bar 200A displayed in the target area is displayed as a menu bar 200A' in the aiming area, the menu bar 200A' in the aiming area is tapped. Then, a drop-down menu 210A corresponding to the menu bar 200A is displayed on the screen of the touch panel 11. In this case, the drop-down menu 210A represents the difference, but the drop-down menu 210A occupies less than 50% of the screen of the touch panel 11. The drop-down menu 210A is thus reset as the target area. In coordination with such resetting of the target area, a drop-down menu 210A' is displayed in the aiming area.

At this time, when a menu item included in the drop-down menu 210A' in the aiming area is tapped, a sub-menu 220B corresponding to the menu item is further displayed on the screen of the touch panel 11. In this case, the sub-menu 220B represents the difference, and the sub-menu 220B occupies less than 50% of the screen of the touch panel 11. The sub-menu 220B is thus reset as the target area. In coordination with such resetting of the target area, a sub-menu 220B' is displayed in the aiming area. Consequently, the menu can be selected in sequence in the order of the menu bar 200A, the menu item in the drop-down menu 210A, and the sub-menu 220B of the menu item.

Application of Correspondence Relation Information

While the correspondence relation between the coordinates of each pixel included in the aiming area and the coordinates of each pixel included in the target area is illustrated and described to be recorded as the correspondence relation information 13b in the first embodiment, the information other than the coordinates between the pixels can be recorded being correlated. For example, the disclosed apparatus can record the correspondence relation information in which pixel values of the partial image displayed in the target area are correlated to the corresponding relation of coordinates between the pixels in the aiming area and in the target area. The disclosed apparatus then updates the record of the correspondence relation information in response to the update of the partial image displayed in the target area made by the OS and application programs executed in the controller 15. Consequently, when the partial image displayed in the target area changes, for example, even when a movie is reproduced or a banner is displayed, the partial image displayed in the aiming area can be synchronized with the partial image displayed in the target area using the correspondence relation information.

Application of Display Timing of Partial Image

While the partial image in the aiming area is illustrated and described to be displayed in real-time when the target area is set up in the first embodiment, the partial image in the aiming area is not necessarily displayed in real-time. For example, the disclosed apparatus can store an image at the time the target area is set up in the storage unit 13, and when a given condition is satisfied, for example, a condition in which a screen is scrolled to an end, and a condition in which an operation to release the display of partial image is received, the disclosed apparatus can display the partial image in the aiming area.

Distribution and Integration

The respective constituent elements of the devices illustrated in the drawings are functionally conceptual and are not necessarily configured physically as illustrated in the drawings. In other words, the specific embodiments of distribution or integration of the devices are not restricted to those illustrated, and the whole or a part thereof can be configured by being functionally or physically distributed or integrated in any unit according to various types of loads and usage. For example, at least one of the functional units out of the receiving unit 15b, the setting unit 15c, the display controller 15d, the recording unit 15e, the converter 15f, and the output unit 15g may be connected via a network as an external device of the tablet terminal 10 and configured as a server that performs an operation receiving service. Furthermore, the receiving unit 15b, the setting unit 15c, the display controller 15d, the recording unit 15e, the converter 15f, or the output unit 15g may be implemented in separate devices and connected via a network to coordinate so as to achieve the functions of the above-described tablet terminal 10.

Operation Receiving Program

The various processes described in the foregoing embodiments can be realized by executing a computer program prepared in advance on a computer such as a personal computer and a work station. The following description explains, with reference to FIG. 12, an example of a computer that executes an operation receiving program which renders the same functions as those in the above-described embodiments.

Figure 12:
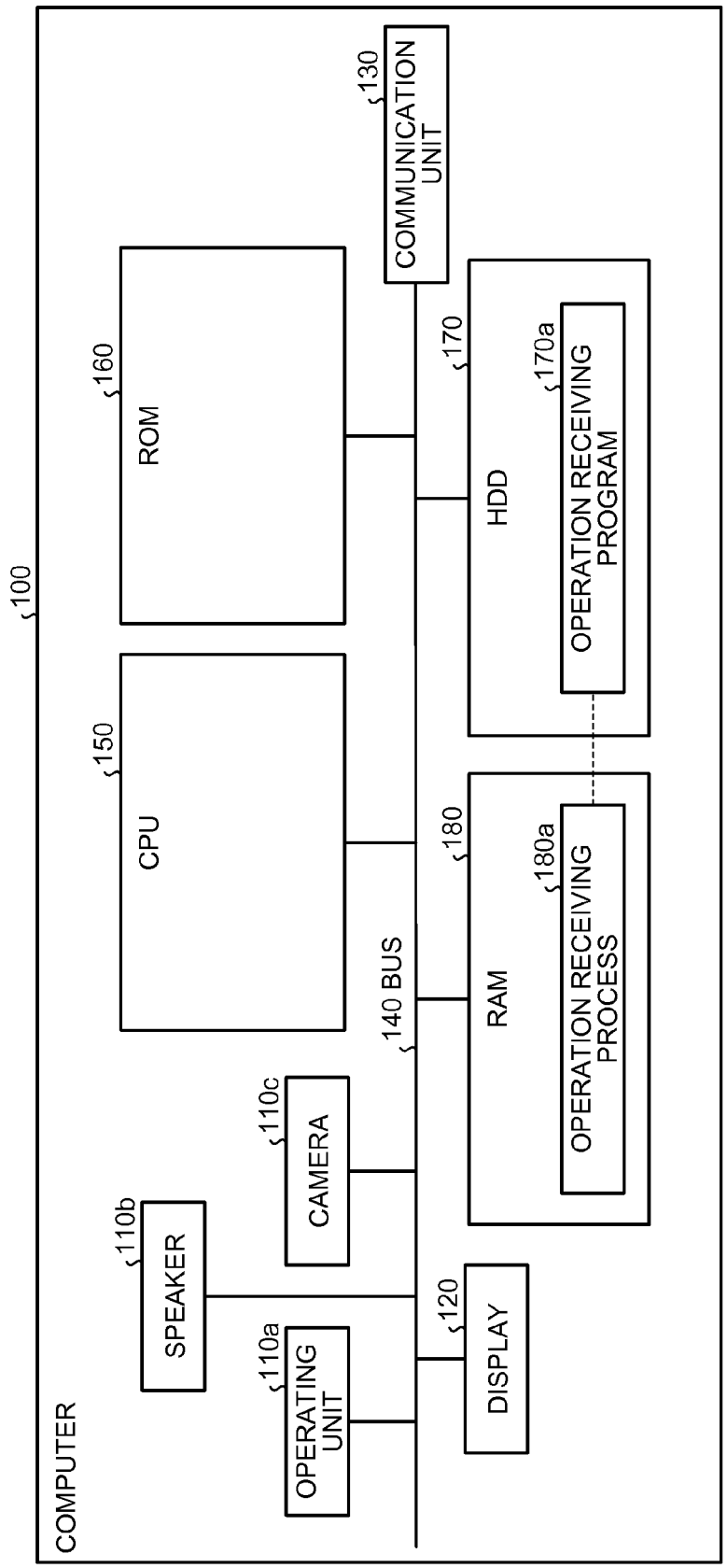
FIG. 12 is a block diagram for explaining an example of a computer that executes an operation receiving program according to the first embodiment and a second embodiment.

FIG. 12 is a block diagram for explaining an example of the computer that executes the operation receiving program in the first and the second embodiments. As illustrated in FIG. 12, a computer 100 includes an operating unit 110a, a speaker 110b, a camera 110c, a display 120, and a communication unit 130. The computer 100 further includes a CPU 150, a ROM 160, an HDD 170, and a RAM 180. The respective units 110 to 180 are connected via a bus 140.

The HDD 170 stores therein in advance, as illustrated in FIG. 12, an operation receiving program 170a that exercises the same functions as those of the receiving unit 15b, the setting unit 15c, the display controller 15d, the recording unit 15e, the converter 15f, and the output unit 15g illustrated in the first embodiment. The operation receiving program 170a may appropriately be distributed or integrated similarly to the respective constituent elements of the receiving unit 15b, the setting unit 15c, the display controller 15d, the recording unit 15e, the converter 15f, and the output unit 15g depicted in FIG. 1. More specifically, as for the respective data stored in the HDD 170, the HDD 170 does not necessarily need to store therein all the data all the time, and the HDD 170 needs to store therein only the data for processing.

The CPU 150 then reads out the operation receiving program 170a from the HDD 170 and loads it to the RAM 180. Consequently, as illustrated in FIG. 12, the operation receiving program 170a functions as an operation receiving process 180a. The operation receiving process 180a appropriately loads various items of data read out from the HDD 170 to an area assigned for the operation receiving process itself on the RAM 180, and based on the various items of data loaded, executes the various processes. The operation receiving process 180a includes the processes executed by the receiving unit 15b, the setting unit 15c, the display controller 15d, the recording unit 15e, the converter 15f, and the output unit 15g depicted in FIG. 1, for example, the process illustrated in FIG. 10. Incidentally, all processing units virtually realized on the CPU 150 do not always have to operate on the CPU 150, and it is sufficient if a processing unit for each process is virtually realized. Then, the CPU 150 executes an image processing program by the use of the RAM 180.

The operation receiving program 170a is not necessarily stored in the HDD 170 or the ROM 160 from the beginning. For example, the program may be stored in a transportable physical medium that is inserted to the computer 100 such as a flexible disk known as an FD, a CD-ROM, a digital versatile disk (DVD), a magneto-optical disk, and an integrated circuit (IC) card. The computer 100 may then acquire the program from these transportable physical media and execute the program. Furthermore, the program may be stored in other computers and servers connected to the computer 100 via a public line, the Internet, a local area network (LAN), a wide area network (WAN), or the like, and the computer 100 may then acquire the program from the foregoing and execute the program.

The tablet terminal according to one aspect of the embodiment disclosed has an effect in that the strain of the eyes of the user can be relieved.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A tablet terminal comprising:
    a memory, and
    a processor coupled to the memory, wherein the processor executes a process comprising:
        receiving a triggering indication to enable a detection result of eye gaze;
        setting a target area in which presence of a target object is assumed on a screen of a touch panel using a detection position of eye gaze;
        displaying a partial image of an image with the target object as displayed in the target area in an aiming area, a touch operation in the aiming area is enabled to be applied to the target area;
        recording a correspondence relation between coordinates of the aiming area and coordinates of the target area in a storage unit;
        converting the coordinates of the aiming area in which the touch operation is received into coordinates projected to the target area using the correspondence relation stored in the storage unit when the touch operation is received in the aiming area; and
        outputting the converted coordinates.

2. The tablet terminal according to claim 1, wherein
the setting includes setting the target area using a detection position of eye gaze before an indication is received by the receiving unit out of the detection results of eye gaze.

3. The tablet terminal according to claim 1, wherein the process further comprising calculating a ratio of difference in an image displayed on the screen of the touch panel before and after coordinates are output at the outputting, wherein
the setting includes resetting an area in which an image that represents the difference is displayed as a target area when the ratio of difference in the image at the calculating is equal to or smaller than a given threshold.

4. The tablet terminal according to claim 1, wherein the target area is located outside a position on the screen that is touchable by a hand holding the tablet terminal, and
the partial image is located within a range from a corner of the screen where the hand holding the tablet terminal is positioned.

5. A computer-readable recording medium having stored therein an operation receiving program causing a computer to execute a process comprising:

receiving a triggering indication to enable a detection result of eye gaze;

setting a target area in which presence of a target object is assumed on a screen of a touch panel using a detection position of eye gaze;

displaying a partial image of an image with the target object as displayed in the target area in an aiming area, a touch operation in the aiming area is enabled to be applied to the target area;

recording a correspondence relation between coordinates of the aiming area and coordinates of the target area in a storage unit;

converting the coordinates of the aiming area in which the touch operation is received into coordinates projected to the target area using the correspondence relation stored in the storage unit when the touch operation is received in the aiming area; and outputting the converted coordinates.

\* \* \* \* \*